United States Patent [19]
Mulligan et al.

[11] Patent Number: 5,922,023
[45] Date of Patent: Jul. 13, 1999

[54] BREAST PROSTHESIS

[75] Inventors: Elisabeth Mulligan, Riedering-Söllhuben; Helmut Wild, Neubeuern, both of Germany

[73] Assignee: Amoena Medizin-Orthopaedie-Technik GmbH & Co., Raubling, Germany

[21] Appl. No.: 08/837,688

[22] Filed: Apr. 30, 1997

[30] Foreign Application Priority Data

May 2, 1996 [DE] Germany ............... 296 07 969 U

[51] Int. Cl.$^6$ .............................................. A61F 2/52
[52] U.S. Cl. ...................................................... 623/7
[58] Field of Search ............................................ 623/7, 8

[56] References Cited

U.S. PATENT DOCUMENTS

| 3,293,663 | 12/1966 | Cronin | 623/8 |
| 3,902,198 | 9/1975 | Rathjen | 623/8 |
| 4,426,742 | 1/1984 | Prahl | 623/7 |
| 4,950,291 | 8/1990 | Mulligan | 623/7 |
| 5,071,433 | 12/1991 | Naestoft et al. | 623/7 |
| 5,352,307 | 10/1994 | Wild | 623/7 |
| 5,584,883 | 12/1996 | Wild | 623/7 |

FOREIGN PATENT DOCUMENTS

| 0320590 A1 | 6/1989 | European Pat. Off. . |
| 0320590A1 | 6/1989 | European Pat. Off. . |
| 0 392 390 | 10/1990 | European Pat. Off. ............. 623/7 |
| 0542119A1 | 5/1993 | European Pat. Off. . |
| 9114512 U | 2/1993 | Germany . |
| 9315935 | 3/1995 | Germany . |
| 2 270 628 | 3/1994 | United Kingdom ............. 623/7 |
| 94/16650 | 8/1994 | WIPO ............. 623/7 |

*Primary Examiner*—Mickey Yu
*Assistant Examiner*—Tram A. Nguyen
*Attorney, Agent, or Firm*—Evenson, McKeown, Edwards & Lenahan, P.L.L.C.

[57] ABSTRACT

The present invention relates to a breast prosthesis comprising two shell-like bodies (2, 3) each welded in between synthetic resin films and consisting of silicone compositions of different softness, wherein the outer body (2) designed according to the form of a breast has a hardness which is adapted to the soft-elastic resiliency of the natural breast tissue, and the inner body (3) has a softer gel-like consistency, wherein the prosthesis is provided with an adhesive layer (4) manufactured to be permanently tacky in its marginal zone on its rear side, a first section (4a) of the adhesive layer (4) being arranged on the outer prosthesis body (2) and a second section (4b) of the adhesive layer (4) being arranged on the inner body (3).

6 Claims, 5 Drawing Sheets

BREAST PROSTHESIS

FIELD OF THE INVENTION

The present invention relates to a breast prosthesis and more, particularly, to a breast prosthesis having two shell-like bodies, each of which is welded in between synthetic resin films and consist of silicone compositions of different softness.

BACKGROUND OF THE INVENTION

Such a breast prosthesis is known from European patent publication 0 320 590 A.

One particular problem occurring with such breast prostheses is ensuring satisfactory attachment to the chest of the user so that they cannot slip.

From German utility model G 91 14 512.0 it is known to provide a prosthesis with an adhesive layer in a marginal zone on its rear side.

It is, however, to be stated that the adhesion and also the duration of the adhesion of such adhesive layers on the body decrease with increasing hardness and strength of the used prosthesis material, as tensional and torsional forces acting upon the prosthesis are directly transmitted to said adhesive layer.

On the other hand, it is unfavorable to attach such an adhesive layer on a material being too soft, as in this case difficulties in the maintenance of the desired form of the prosthesis arise, and, furthermore, tensional and peeling forces occurring when the prosthesis is removed, cannot be effectively absorbed when the material is too soft.

SUMMARY OF THE INVENTION

Accordingly one object of the invention is to develop a breast prosthesis of the type initially mentioned such that it may be removably fastened in a simple way directly on the skin of a user, wherein the duration of adhesion of the prosthesis is to be increased.

In order to fulfil this object, a breast prosthesis having two shell-like bodies, each welded in between synthetic resin films and consisting of silicone compositions of different softness, wherein the outer body designed according to the form of the breast has a hardness which is adapted to the soft-elastic resiliency of the natural breast tissue, and the inner body has a softer gel-like consistency is designed so that on its rear side in a marginal zone it is provided with a permanent adhesive layer, wherein a first section of the adhesive layer is arranged on the outer prosthesis body and a second section of the adhesive layer is arranged on the inner prosthesis body.

By arranging the adhesive layer in the manner that a first section is connected with the harder, outer prosthesis body and a second section is connected with the softer, inner prosthesis body, forces caused by movements of the user can be absorbed advantageously by the breast prosthesis as a whole, so that no excessive load is applied to the adhesive layer. Thereby the longevity of the adhesive layer and a long duration of adhesion are guaranteed.

The outer prosthesis body may perform rotary movements to a certain extent about the section in which it is connected to the adhesive layer, as the substantially softer inner prosthesis body lying under the outer prosthesis body is resiliently deformable to a greater extent. Furthermore, the inner prosthesis body may be adapted to irregularities on the skin surface of the user due to its flexibility and softness, whereby an improved static friction can be obtained.

It is an advantage that the surface area portion of the first section amounts up to approximately ¼ through ⅓ of the entire surface area of the adhesive layer.

It is convenient for the layer to consist of separate adhesive zones spaced from each other.

It is an advantage if the permanent adhesive layer is designed encircling the arrangement.

In accordance with a further advantageous development, the breast prosthesis is provided with an encompassing groove in its marginal part on its rear side, in which groove the adhesive layer is embedded.

It is convenient for the adhesive layer to be protected by a cover film arranged thereon. This film is removed prior to putting on the breast prosthesis.

One working embodiment of the invention will now be described in the following with reference to the accompanying drawings.

DETAILED DESCRIPTION OF THE DRAWINGS

Figure 1:
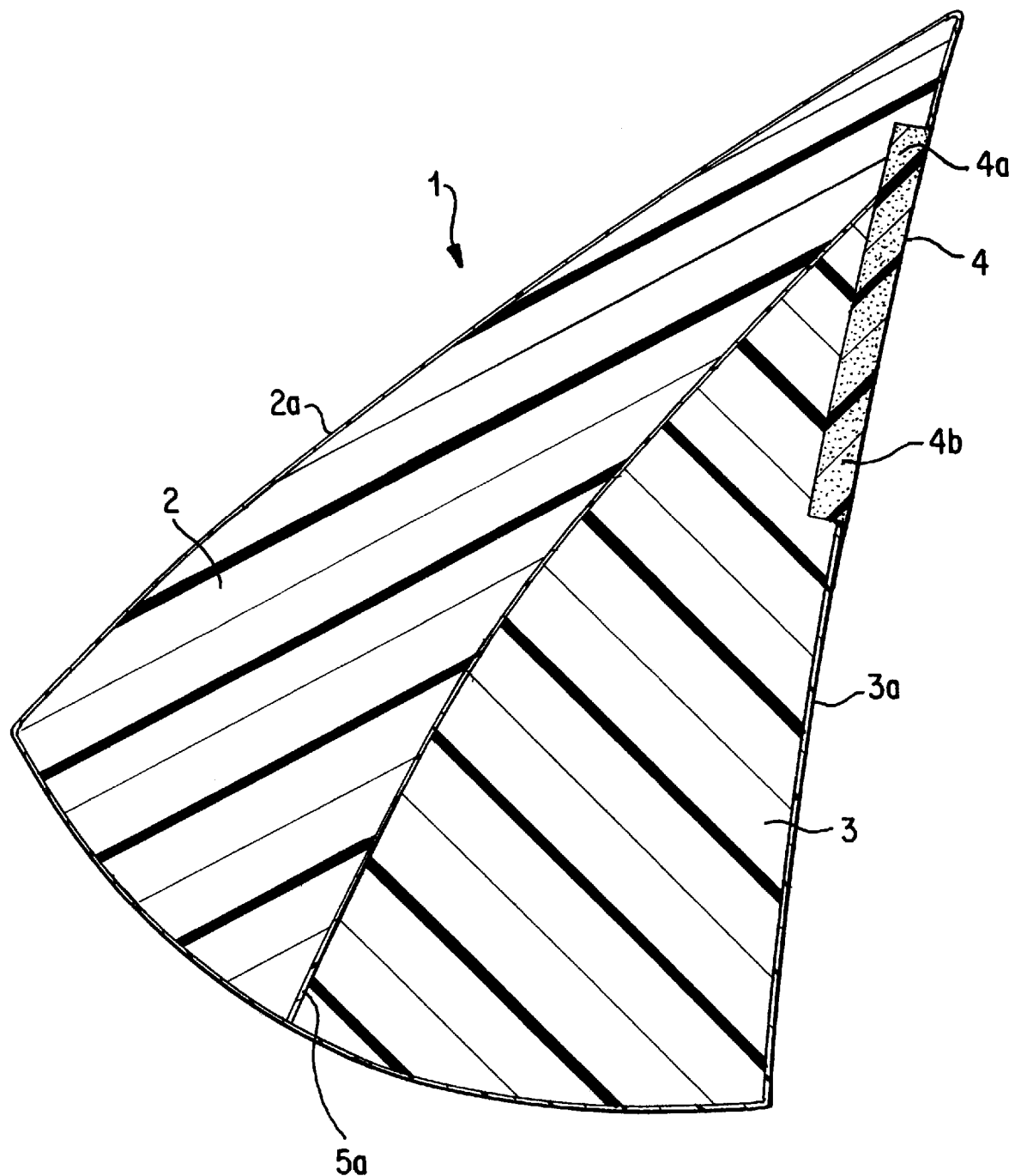
FIG. 1 is a lateral sectional view of a first embodiment of the breast prosthesis according to the invention.

The breast prosthesis shown in FIG. 1 consists of an outer body 2, for instance made of a two-component, addition cross-linked soft elastic silicone rubber mass, and of a body 3 forming the largest part of the rear side of the prosthesis and consisting of a softer material with a gel-like consistency, for instance a two-component, addition cross-linked silicone rubber. On their outer surfaces, the two bodies 2, 3 are enclosed within synthetic resin films 2a, 3a, for instance polyurethane films, and are separated from each other by an intermediate film 5a. The shell-like bodies are welded in between the synthetic resin films.

On the rear side of the breast prosthesis 1 there is provided an adhesive layer 4. A first section 4a of said adhesive layer is connected with the outer prosthesis body 2 designed in the form of a breast, whereas a second section 4b of the adhesive layer rests against the inner body 3. The adhesive layer can be manufactured to be permanently tacky.

Said arrangement of the adhesive layer ensures an optimal attachment of the breast prosthesis at the skin of the user.

Forces caused by movements of the user and acting upon the breast prosthesis may be absorbed by the adhesive layer due to the—in a way—'articulated' or 'flexible' design of the breast prosthesis. Said 'flexibility' is obtained by the fact that due to the very soft and gel-like consistency of the prosthesis body 3 a resilient rotary movement of the outer prosthesis body 2 with the section 4a of the adhesive layer as turning center is possible. Thereby it is guaranteed that in particular section 4b of the adhesive layer is only strained to a small extent so that the adhesion on the body of the user is not affected. Thus, the duration of adhesion of a prosthesis body according to the invention at the body of the user is increased.

It is an advantage that the portion of the section of the adhesive layer arranged on the harder and more solid silicone amounts up to approximately ¼ through ⅓ of the entire surface area of the adhesive layer. Thereby it is guaranteed that tensional and peeling forces occurring during the removal of the prosthesis may be absorbed via said layer.

At the same time, the second prosthesis body 3 having the gel-like consistency enables an optimal adaptation of the adhesive layer 4 to the irregularities of the skin of the user, for instance to scars caused by an operation.

As is also to be seen in FIG. 1, the adhesive layer 4 is provided in a groove formed at the inner side of the prosthesis body, so that the outer side of the adhesive layer 4 is flush with the rear side of the prosthesis. By said measure not only the wearing comfort for the user is increased, but also an improved adhesion of the adhesive layer is obtainable.

Figure 2:
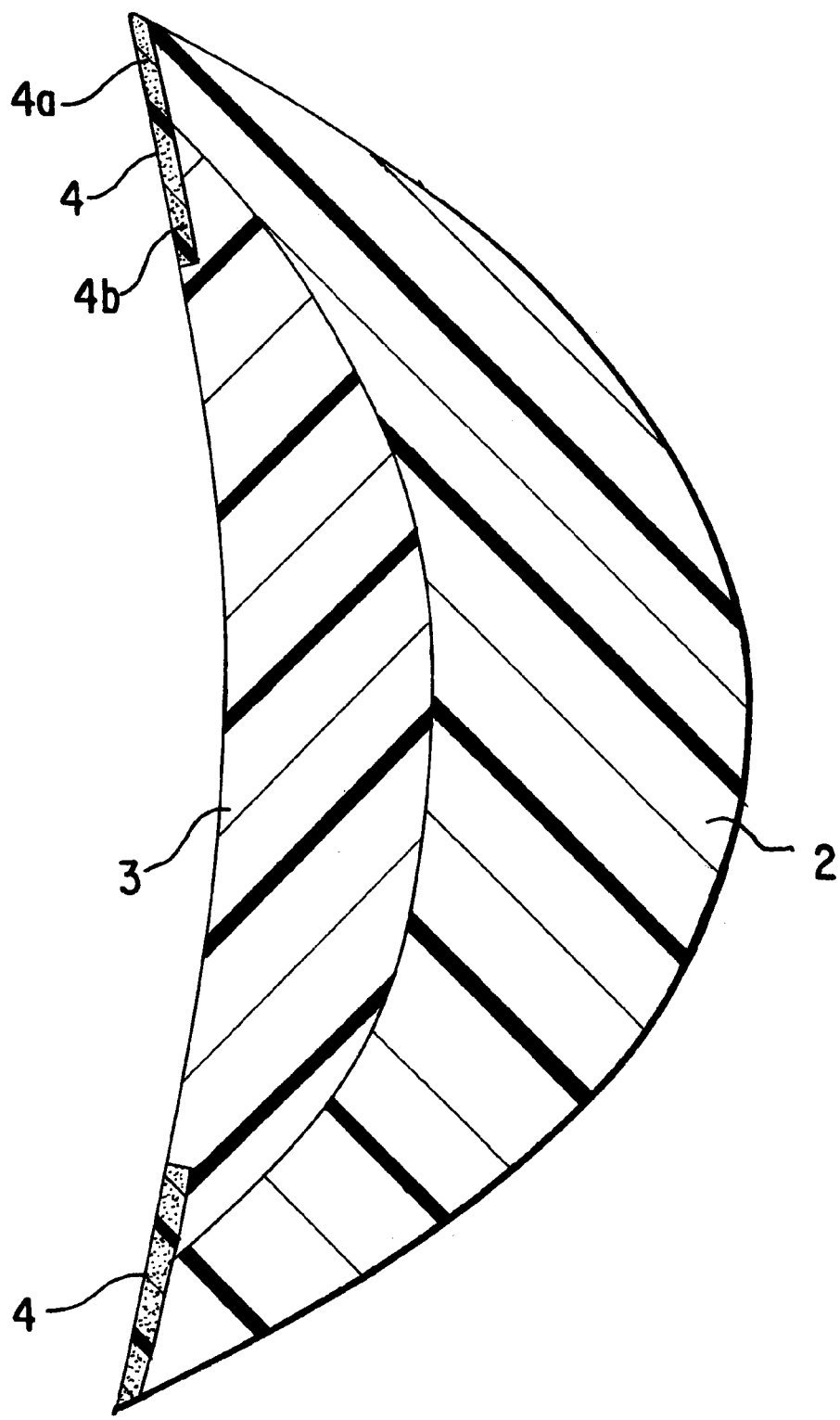
FIG. 2 is a lateral sectional view of a second embodiment of the breast prosthesis according to the invention.

In FIG. 2, another embodiment of the inventive breast prosthesis is shown. The difference to the embodiment of FIG. 1 lies in the fact that here the adhesive layer 4 has an encircling form.

Figure 3:
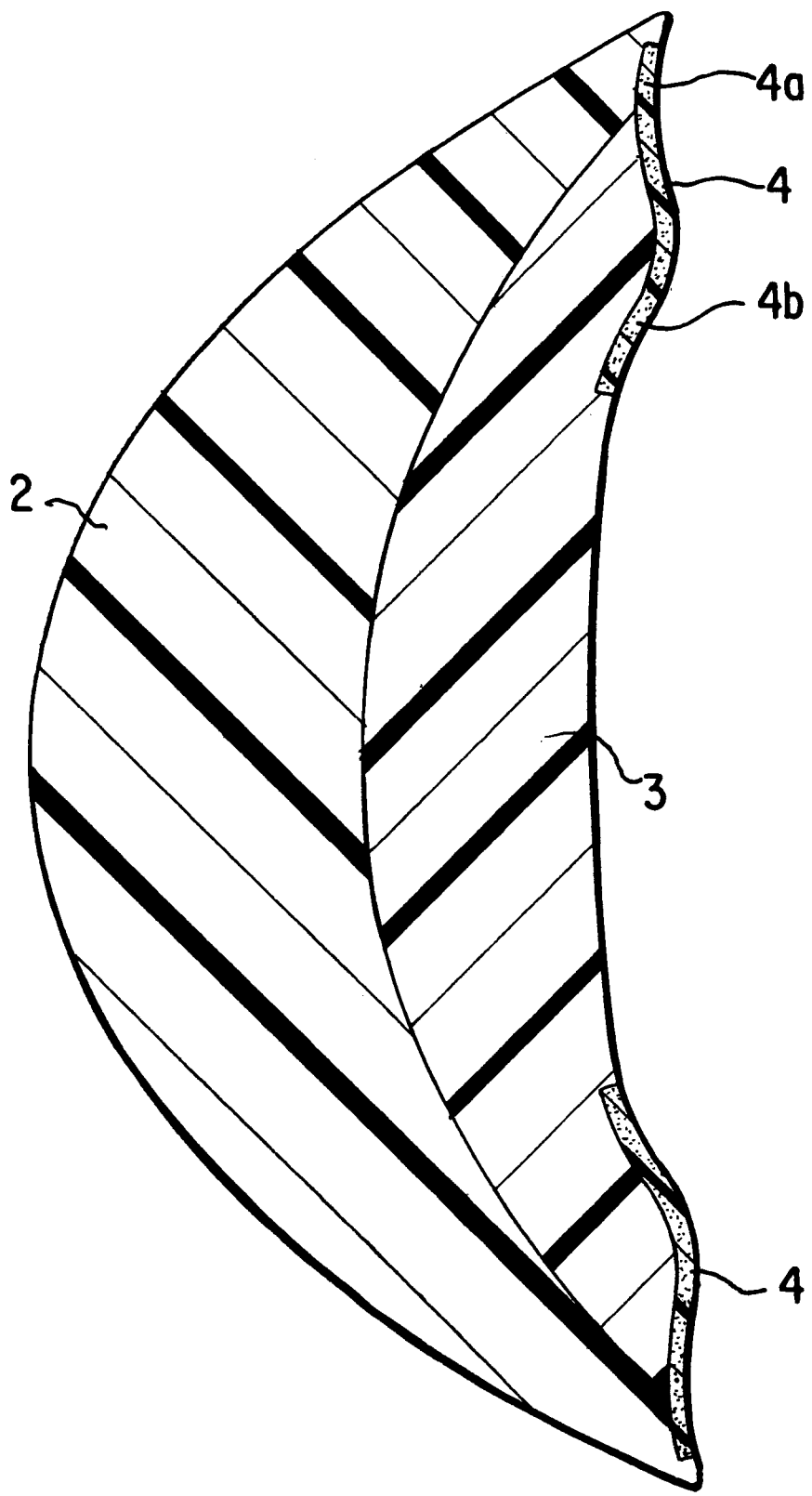
FIG. 3 is a lateral sectional view of a third embodiment of the breast prosthesis according to the invention.

FIG. 3 shows a further embodiment of the breast prosthesis according to the invention. It can be seen that the outer section of the inner prosthesis body 3 is designed to protrude outwardly in a wave-like form. The inner section 4*b* of the adhesive layer 4 has a correspondingly wave-like form. By the section 4*b* protruding in a wave-like form, an increased mobility and adaptability of said prosthesis section is guaranteed, so that said prosthesis section can be adapted to a scar tissue of the user in a particularly advantageous manner.

Figure 4:
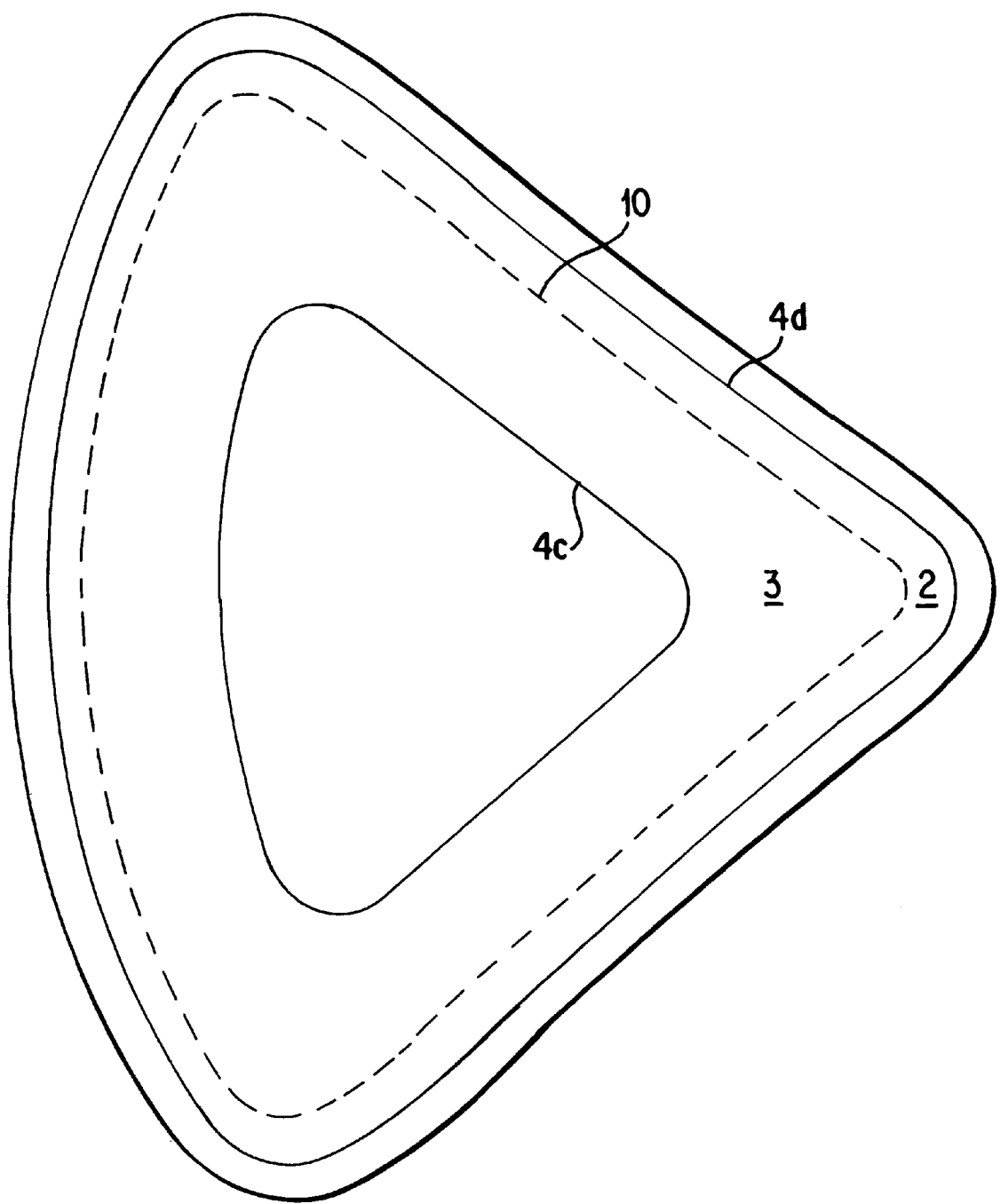
FIG. 4 is a view of the rear side of a breast prosthesis provided with an encircling or peripheral adhesive layer.

Finally, in FIG. 4 the preferred dimensioning of the adhesive layer 4 on the rear side of the prosthesis bodies 2, 3 is indicated diagrammatically. Herein, the continuous lines 4*c* and 4*d* represent the inner and the outer margin of the adhesive layer. The broken line 10 indicates the border between the outer and the inner prosthesis bodies 2, 3. The adhesive may be applied to the surface of the rear side of the prosthesis body or encompassed in a groove therein.

Figure 5:
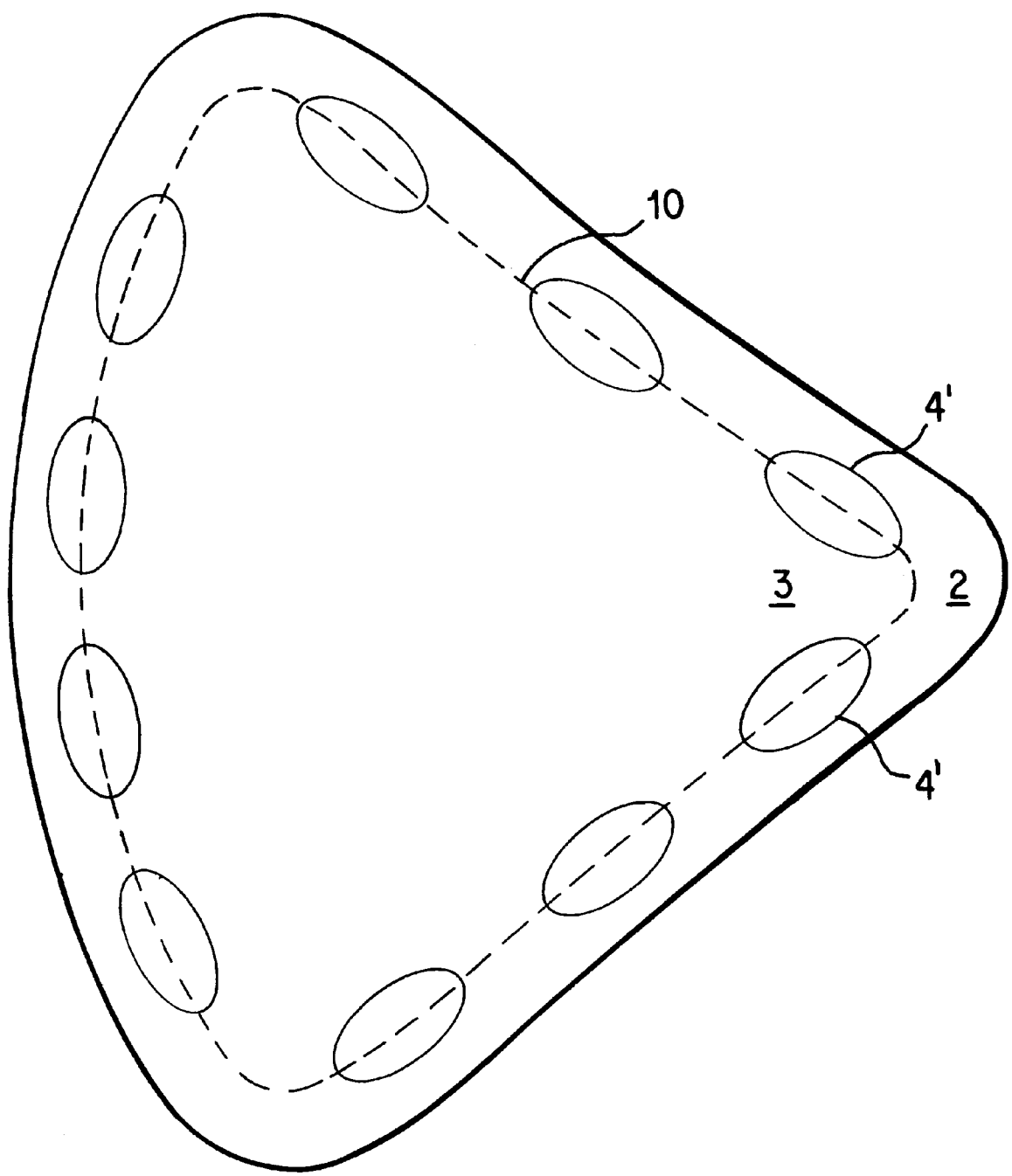
FIG. 5 is a view of the rear side of a breast prosthesis provided with adhesive zones which are separated from each other.

FIG. 5 shows, similarly to FIG. 4, a rear side of a breast prosthesis of the invention in which adhesive zones 4' are separated from each other, and are either disposed on the surface of the rear side of the breast prosthesis or the adhesive zones are disposed in grooves therein.

What is claimed is:

1. A breast prosthesis, comprising:

two shell-like bodies, one of the two shell-like bodies being an outer body and the other being an inner body, each one of said bodies being enclosed within a synthetic resin film and being formed of silicone compositions, each one of said bodies having a different softness, wherein the outer body designed according to the form of a breast has a hardness which is adapted to the soft-elastic resiliency of natural breast tissue, and wherein the inner body has a softer gel-like consistency; and wherein a permanent adhesive layer is formed on a rear side in a marginal zone of the prosthesis, said permanent adhesive layer having a first section located on the outer body and a second section located on the inner body.

2. The breast prosthesis as claimed in claim 1, wherein the adhesive layer manufactured to be permanently tacky comprises adhesive zones which are separated from each other, each zone overlapping both the outer and inner bodies.

3. The breast prosthesis as claimed in claim 1, wherein the permanent adhesive layer has an encircling form.

4. The breast prosthesis as claimed in claim 1, wherein the prosthesis is provided with an encompassing groove in the marginal zone on the rear side, in which the permanent adhesive layer is embedded.

5. The breast prosthesis as claimed in claim 1, wherein the surface area portion of the first section of the adhesive layer amounts approximately up to ¼ through ⅓ of the entire surface area of the adhesive layer.

6. The breast prosthesis according to claim 1, wherein the permanent adhesive layer has a continuous surface, the first section of which overlaps the outer body and the second section overlaps the inner body.

* * * * *